US00PP28852P2

(12) United States Plant Patent
Taquet

(10) Patent No.: US PP28,852 P2
(45) Date of Patent: Jan. 2, 2018

(54) ***PENSTEMON* PLANT NAMED 'BALMIBEPRO'**

(50) Latin Name: ***Penstemon* hybrid**
Varietal Denomination: Balmibepro

(71) Applicant: Ball Horticultural Company, West Chicago, IL (US)

(72) Inventor: Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 9 days.

(21) Appl. No.: 15/330,153

(22) Filed: Aug. 16, 2016

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Susan McCormick Ewoldt
(74) *Attorney, Agent, or Firm* — Audrey Charles

(57) ABSTRACT

A new and distinct cultivar of *Penstemon* plant named 'Balmibepro', characterized by its deep purplish-red and creamy-white colored flowers, blooming from late spring through late summer, medium green-colored foliage, and moderately vigorous, upright growth habit, is disclosed.

1 Drawing Sheet

Latin name of genus and species of plant claimed: *Penstemon* hybrid.
Variety denomination: 'Balmibepro'.

BACKGROUND OF THE INVENTION

The present invention relates to a new and distinct cultivar of *Penstemon* plant botanically known as *Penstemon* hybrid and hereinafter referred to by the cultivar name 'Balmibepro'.

The new cultivar originated in a controlled breeding program in Venhuizen, the Netherlands during August 2013. The objective of the breeding program was the development of *Penstemon* cultivars having large flowers and a long flowering season.

The new *Penstemon* cultivar is the result of cross-pollination. The female (seed) parent of the new cultivar is the proprietary *Penstemon* hybrid breeding selection coded D2330-1, not patented, characterized by its red and creamy-white colored flowers of unilateral arrangement, medium green-colored foliage, and moderately vigorous, upright growth habit. The male (pollen) parent of the new cultivar is the proprietary *Penstemon* hybrid breeding selection coded D2316-2, not patented, characterized by its red-colored flowers, medium green-colored foliage, and moderately vigorous, upright growth habit. The new cultivar was discovered and selected as a single flowering plant within the progeny of the above stated cross-pollination during July 2014 in a controlled environment in Venhuizen, the Netherlands.

Asexual reproduction of the new cultivar by terminal stem cuttings since July 2014 in Venhuizen, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmibepro' as a new and distinct cultivar of *Penstemon* plant:

1. Deep purplish-red and creamy-white colored flowers;
2. Medium green-colored foliage; and
3. Moderately vigorous, upright growth habit.

Plants of the new cultivar differ from plants of the female parent primarily in arrangement of flowers on rachis. Plants of the new cultivar differ from plants of the male parent primarily in flower color.

Of the many commercially available *Penstemon* cultivars, the most similar in comparison to the new cultivar is 'Cha Cha Cherry', U.S. Plant Pat. No. 28,163. However, in comparison, plants of the new cultivar differ from plants of 'Cha Cha Cherry' in at least the following characteristics:

1. Plants of the new cultivar have larger flowers than plants of 'Cha Cha Cherry'; and
2. Plants of the new cultivar have a corolla tube color different from plants of 'Cha Cha Cherry'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balmibepro'. The plants were approximately 17 weeks old and grown in 1.7 gallon containers. Plants were finished outdoors for 7 weeks in West Chicago, Ill. Plants were given two pinches prior to transplant.

DETAILED BOTANICAL DESCRIPTION

Figure 1:
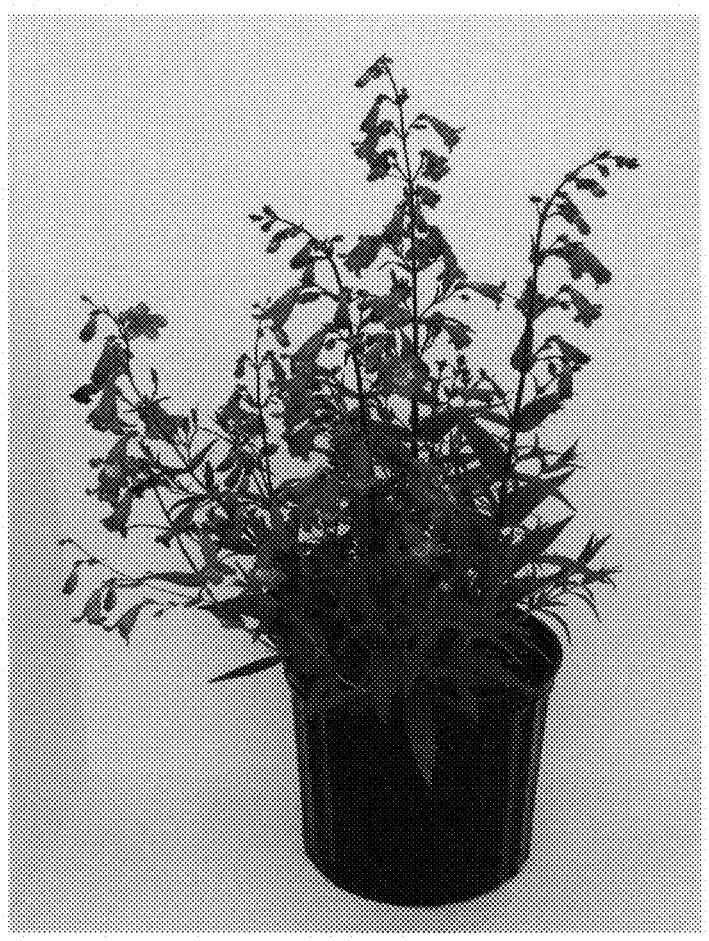
FIG. 1 illustrates a side view of the overall growth and flowering habit of 'Balmibepro'.
Figure 2:
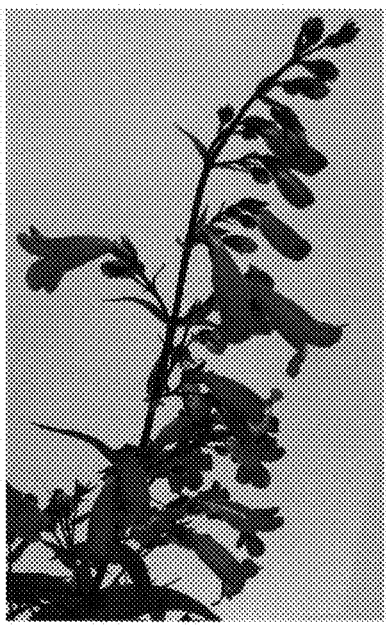
FIG. 2 illustrates a close-up view of an inflorescence of 'Balmibepro'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Chicago, Ill.

The following descriptions and measurements describe plants produced from cuttings from stock plants and grown under conditions comparable to those used in commercial practice. The plants were grown utilizing a soilless growth medium in 1.7 gallon containers for approximately 17 weeks. Plants were given two pinches prior to transplant. For approximately 8 weeks after transplant, greenhouse temperatures were maintained at approximately 60° F. (15.6° C.) during the day and approximately 55° F. (12.8° C.) during the night. For the final 7 weeks, plants were grown outside in West Chicago, Ill. No supplemental lighting was provided. Measurements and numerical values represent averages of typical plants.

Botanical classification: *Penstemon* hybrid cultivar Balmibepro.

Parentage:

*Female parent*.—Proprietary *Penstemon* hybrid breeding selection coded D2330-1, not patented.

*Male parent*.—Proprietary *Penstemon* hybrid breeding selection coded D2316-2, not patented.

Propagation:

*Type cutting*.—Terminal stem.

*Time to initiate roots*.—Approximately 10 to 12 days.

*Time to produce a rooted cutting*.—Approximately 5 to 6 weeks.

*Root description*.—Fine to medium, fibrous white to light brown in color.

*Rooting habit*.—Freely branching.

Plant description:

*Commercial crop time*.—Approximately 10 to 12 weeks from a rooted cutting to finish in a 15 cm pot.

*Growth habit and general appearance*.—Perennial; moderately vigorous, upright growth habit.

*Hardiness*.—USDA Zones 5 to 9.

*Size*.—Height from soil level to top of plant plane: Approximately 59.0 cm. Width: Approximately 33.0 cm.

*Branching habit*.—Freely branching. Pinching enhances lateral branching. Quantity of branches per plant: Approximately 3 main basal branches and approximately 24 lateral branches.

*Branch*.—Shape: Round in cross section. Strength: Strong. Length: Approximately 31.0 cm. Diameter: Approximately 5.0 mm. Length of central internode: Approximately 3.5 cm. Texture: Densely pubescent with very short hairs. Color of young stem: 145B with an overlay of 187A. Color of mature stem: 145A with an overlay of 187A.

Foliage description:

*General description*.—Quantity of leaves per branch: Approximately 20. Fragrance: None detected. Form: Simple. Arrangement: Opposite and decussate.

*Leaves*.—Aspect: Acute angle to stem with tips downward turning. Shape: Narrowly ovate to narrowly elliptic. Margin: Shallowly serrate. Apex: Acute. Base: Sessile. Venation pattern: Pinnate. Length of mature leaf: Approximately 9.0 cm. Width of mature leaf: Approximately 2.5 cm. Texture of upper and lower surfaces: Glabrous. Color of upper surface of young and mature foliage: NN137A with venation of 146D. Color of lower surface of young and mature foliage: Closest to but lighter than NN137D with venation of 146D.

Flowering description:

*Flowering habit*.—'Balmibepro' is freely flowering under outdoor growing conditions blooming from late spring through late summer.

*Lastingness of individual floret*.—Approximately 6 to 7 days.

Inflorescence description:

*General description*.—Type: Terminal raceme, not persistent, multilateral arrangement. Quantity of open inflorescences per plant: Approximately 8. Fragrance: None detected. Length or height of inflorescence: Approximately 36.5 cm. Width of inflorescence: Approximately 10.5 cm. Quantity of fully-open flowers per inflorescence: Approximately 12.

*Peduncle*.—Strength: Strong. Aspect: Erect. Length: Approximately 4.0 cm. Diameter: Approximately 4.0 mm. Texture: Densely glandular pubescent. Gland color: Colorless, transparent. Color: 145A with a heavy overlay of 187A.

Flower description:

*Type*.—Single, zygomorphic.

*Bud*.—Rate of opening: Generally takes 3 to 4 days for bud to progress from first color to fully open flower.

*Bud just before opening*.—Shape: Obovoid. Length: Approximately 1.5 cm. Diameter: Approximately 6.0 mm. Texture: Densely glandular pubescent. Gland color: Colorless, transparent. Color: Calyx of 137A with a heavy overlay of 187A; petals of 59A to 59B.

*Corolla*.—Shape: Bilabiate, upper lip of two lobes and lower lip having three lobes. Width: Approximately 2.3 cm. Length: Approximately 2.0 cm. Depth: Approximately 3.6 cm.

*Upper lip lobes*.—Shape: Ovate. Margin: Entire. Apex: Rounded. Length from throat: Approximately 8.0 mm. Width: Approximately 7.0 mm. Texture of upper surface: Glabrous. Texture of lower surface: Sparsely glandular pubescent. Gland color: Colorless, transparent. Color of upper surface when first and fully open: 59B with base of NN155D, narrow border of 64B where color transitions. Color of lower surface when first and fully open: 59A.

*Lower lip lobes*.—Shape: Ovate. Margin: Entire. Apex: Rounded. Length from throat of central lobe: Approximately 6.0 mm. Width of central lobe: Approximately 7.0 mm. Length from throat of lateral lobes: Approximately 7.0 mm. Width of lateral lobes: Approximately 8.0 mm. Texture of upper surface: Glabrous. Texture of lower surface: Moderately glandular pubescent. Gland color: Colorless, transparent. Color of upper surface when first and fully open: 59B with base of NN155D, narrow border of 64B where color transitions. Color of lower surface when first and fully open: 59A.

*Corolla tube*.—Length: Approximately 2.7 cm. Width: Approximately 1.2 cm. Texture of inner surface: Glabrous. Texture of outer surface: Moderately pubescent. Color of inner surface: NN155A with venation of 59A. Color of outer surface: Between 59B and 59C.

*Calyx*.—Shape: Cupped. Length: Approximately 7.0 mm. Diameter: Approximately 5.0 mm.

*Sepals*.—Quantity per flower: 5. Apex: Acute. Base: Truncate. Length: Approximately 7.0 mm. Width: Approximately 2.0 mm. Texture of inner surface: Glabrous. Texture of outer surface: Moderately glandular pubescent. Gland color: Colorless, transparent. Color of inner surface: 144A. Color of outer surface: 137A with an overlay of 187A.

*Pedicel*.—Strength: Strong, flexible. Aspect: At an acute angle. Length: Approximately 5.0 mm. Diameter: Approximately 1.0 mm. Texture: Densely glandular pubescent. Gland color: Colorless, transparent. Color: 187A.

*Reproductive organs*.—Androecium: Stamen quantity: 5 per flower, one lacking an anther, connate by filaments. Stamen length: Approximately 2.7 cm. Filament length: Approximately 2.6 cm. Filament length of fixed portion: Approximately 1.0 cm. Filament color: NN155B. Anther shape: Horseshoe-like. Anther length: Approximately 3.0 mm. Anther color: 72B. Pollen amount: Abundant. Pollen color: NN155D. Gynoecium: Pistil quantity: 1 per flower. Pistil length: Approximately 3.0 cm. Stigma shape: Conical. Stigma length: Less than 1.0 mm. Stigma color: NN155D. Style length: Approximately 2.6 cm. Style color: NN155D with a faint overlay of 72B. Ovary length: Approximately 4.0 mm. Ovary color: N144C.

Seed and fruit production: Neither seed nor fruit production has been observed.

Disease and pest resistance: Resistance to pathogens and pests common to *Penstemon* has not been observed.

What is claimed is:

1. A new and distinct cultivar of *Penstemon* plant named 'Balmibepro', substantially as herein illustrated and described.

* * * * *